United States Patent
Iversen et al.

(10) Patent No.: US 7,754,238 B2
(45) Date of Patent: Jul. 13, 2010

(54) DELIVERY OF MICROPARTICLE-CONJUGATED DRUGS FOR INHIBITION OF STENOSIS

(75) Inventors: Patrick L. Iversen, Corvallis, OR (US); Nicholas Kipshidze, New York, NY (US)

(73) Assignee: AVI BioPharma, Inc., Corvallis, OR (US)

( * ) Notice: Subject to any disclaimer, the term of this patent is extended or adjusted under 35 U.S.C. 154(b) by 782 days.

(21) Appl. No.: 10/190,419

(22) Filed: Jul. 2, 2002

(65) Prior Publication Data

US 2003/0206960 A1 Nov. 6, 2003

Related U.S. Application Data

(63) Continuation-in-part of application No. 10/138,589, filed on May 3, 2002, now abandoned.

(51) Int. Cl.
  *A61K 9/127* (2006.01)
  *A61K 9/48* (2006.01)
(52) U.S. Cl. .................. 424/450; 424/451; 424/9.5
(58) Field of Classification Search ................ 424/400, 424/9.52, 9, 450, 451, 9.5; 514/156
See application file for complete search history.

(56) References Cited

U.S. PATENT DOCUMENTS

| 5,288,711 | A | * | 2/1994 | Mitchell et al. | ............... 514/56 |
| 5,516,781 | A | | 5/1996 | Morris et al. | |
| 5,756,673 | A | * | 5/1998 | Somenshein et al. | ......... 530/350 |
| 6,117,858 | A | * | 9/2000 | Porter et al. | ................. 514/156 |
| 6,245,747 | B1 | * | 6/2001 | Porter et al. | ................... 514/44 |
| 6,273,913 | B1 | * | 8/2001 | Wright et al. | .............. 623/1.42 |
| 6,369,039 | B1 | * | 4/2002 | Palasis et al. | ................. 514/44 |

FOREIGN PATENT DOCUMENTS

| WO | WO 98/00172 | * | 1/1998 |
| WO | WO 00/02588 A1 | | 1/2000 |
| WO | WO 00/42988 A1 | | 7/2000 |
| WO | WO 00/44897 A1 | | 8/2000 |

OTHER PUBLICATIONS

Chong, P.H. and Cheng, J.W.M., "Early Experiences and Clinical Implications of Drug-Eluting Stents: Part 1", *Ann. Pharmacother.* 38:661-9 (2004).

Gregory, C.R. et al., "Rapamycin inhibits arterial intimal thickening caused by both alloimmune and mechanical injury. Its effect on cellular, growth factor, and cytokine response in injured vessels", *Transplantation* 55(6):1409 (1993), Abstract Only.

Klugherz, B.D. et al., "Intramural Kinetics of Sirolimus Eluted from an Intracoronary Stent", *Circulation* 102 (18 Supplement):II.733 (2000).

Suzuki, T. et al., "Stent-Based Delivery of Sirolimus Reduces Neointimal Formation in a Porcine Coronary Model", *Circulation* 104:1188-1193 (2001).

Marx, S.O., M.D. and Marks, A. R., M.D., "The Development of Rapamycin and Its Application to Stent Restenosis", *Circulation* 104:852-855 (2001).

Bennett, M. R. and O'Sullivan, M., "Mechanisms of angioplasty and stent restenosis: implications for design of rational therapy", *Pharmacology & Therapeutics* 91:149-166 (2001).

Badimon, L. et al. Cell biology of restenosis post-angioplasty. *Zeitschrift fur Kardiologie* 84 Suppl 4: 45-9 (1995), abstract only.

Bauters, C. et al. Proto-oncogene expression in rabbit aorta after wall injury. First marker of the cellular process leading to restenosis after angioplasty? *European Heart Journal* 13(4):556-9 (1992).

Bennett, M.R. et al. Inhibition of vascular smooth muscle cell proliferation in vitro and in vivo by c-myc antisense oligodeoxynucleotides. *J. Clinical Investigation* 93(2):820-8 (1994).

Forte, A. et al. Molecular analysis of arterial stenosis in rat carotids. *J. Cellular Physiology* 186(2):307-313 (2001).

Klugherz, B.D. et al. Twenty-eight-day efficacy and pharmacokinetics of the sirolimus-eluting stent. *Coronary Artery Disease* 13(3)183-8 (May 2002).

(Continued)

*Primary Examiner*—Michael G Hartley
*Assistant Examiner*—Micah-Paul Young
(74) *Attorney, Agent, or Firm*—Seed IP Law Group PLLC

(57) ABSTRACT

Administration of a formulation comprising a antirestenotic compound conjugated to a microparticle carrier is effective to inhibit stenosis formation in a blood vessel. Such stenosis typically results, in the absence of treatment, from trauma to a vessel, such as an incision, excessive pressure, an angioplasty procedure and/or stent implantation. The antirestenotic compound is typically an antiproliferative, immunosuppressive, or antiinflammatory drug, such as rapamycin, tacrolimus, paclitaxel, dexamethasone, or an active analog or derivative, an antisense oligonucleotide, or combinations thereof. The microparticle carrier comprises a suspension of gas-filled microbubbles or biocompatible polymeric microparticles, in a pharmaceutically acceptable liquid vehicle, and is effective to deliver the conjugated therapeutic to the site of vessel injury.

18 Claims, 1 Drawing Sheet

OTHER PUBLICATIONS

Moses, J.W. et al. Perspectives of drug eluting stents: the next revolution. *Am J Cardiovasc Drugs* 2(3):163-72 (2002).

Moses, J.W., Leon, M.B., Popma, J.J. et al. Sirolimus-eluting stents versus standard stents in patients with stenosis in a native coronary artery. *NEJM* 349:1315-23 (2003).

Regar, E., Sianos, G., Serruys, P.W. Stent development and local drug delivery. *Br Med Bull* 59:227-48 (2001).

Schmelzle, T. and Hall, M.N. TOR, a central controller of cell growth. *Cell* 103:253-262 (2000).

Topol, E.J: and Serruys, P.W. Frontiers in interventional cardiology. *Circulation* 98:1802-20 (1998).

Weiser-Evans, M.C.M. et al. Transient reexpression of an embryonic autonomous growth phenotype by adult carotid artery smooth muscle cells after vascular injury. *J. Cellular Physiology* 182:12-23 (2000).

Kent, K.C. et al., Ann. Vasc. Surg. 18(2): 135-7, (2004).

Gallo et al., *Circulation*, 99:2164-2170 (1999).

Kipshidze et al., *Catherization and Cardiovascular Interventions*, 64:389-394 (2005).

International Search Report for PCT/US03/13892.

Bakhtiar et al., "Studies on Non-covalent Associations of Immunosuppressive Drugs with Serum Albumin Using Pneumatically Assisted Electrospray Ionization Mass Spectrometry," *Rapid Communications in Mass Spectrometry*, 9:240-244, 1995.

Jankowski, R. J. et al., "Albumin Microbubbles Preferentially Adhere to the Extracellular Matrix of Inflamed Human Coronary Endothelium," *J. Am. Coll. Cardiol.* 27(2 Suppl. 1):298A, 1996.

Hiser, W. et al., "Non-Invasive Inhibition of Carotid Artery Neointimal Formation and Vascular Remodeling Following Balloon Injury by Treatment with Intravenous Antisense to the c-myc Protooncogene Bound to Perfluorocarbon Microbubbles," *Circulation* 98(17Suppl):I291-292, 1998.

Porter, T. et al., "Non-invasive Prevention of Lumen Area Narrowing Following Coronary Balloon Injury with Intravenous Antisense to the c-myc Protooncogene Bound to Perfluorocarbon Microbubbles," *Circulation* 98(17 Suppl):I503, 1998.

Clay, C. et al., "New Insights into Mechanisms of Albumin Microbubble Adhesion to Coronary Endothelium Using Chemically Modified Microbubbles," *J. Am. Coll. Cardiol.* 33(2 Suppl. 1):407A, 1999.

Lindner, J. R. et al., "Microbubble Persistence in the Microcirculation During Inflammation is Due to their Adherence to Activated Leukocytes," *J. Am. Coll. Cardiol.* 33(2 Suppl. 1):407A-408A, 1999.

Porter, T. R. et al., "Intravenous Antisense Administered Bound to Perfluorocarbon Exposed Sonicated Dextrose Albumin Microbubbles Inhibits Stenosis Formation Following Coronary Balloon Injury," *Circulation* 100(18 Suppl):365, 1999.

Kipshidze, N. et al., "Local Delivery of c-myc Neutrally Charged Antisense Oligonucleotides With Transport Catheter Inhibits Myointimal Hyperplasia and Positively Affects Vascular Remodeling in the Rabbit Balloon Injury Model," *Catheterization and Cardiovascular Interventions* 54:247-256, 2001.

Kipshidze, N. et al., "Selective Systemic Delivery of Rapamycin by Using Perfluorobutane Gas Microbubble Carrier Reduces Neointimal Formation in Stented Porcine Coronary Arteries," *The American Journal of Cardiology* 92(6Suppl 1), 2003.

\* cited by examiner

DELIVERY OF MICROPARTICLE-CONJUGATED DRUGS FOR INHIBITION OF STENOSIS

This application is a continuation-in-part of U.S. Ser. No. 10/138,589 filed on May 3, 2002, now abandoned which is incorporated herein in its entirety by reference.

FIELD OF THE INVENTION

The present invention relates to methods of treating or preventing hyperproliferative disease, e.g. stenosis, in blood vessels, and in particular to preventing stenosis following vascular injury, by delivery of a microparticle-conjugated antirestenotic drug, such as rapamycin, to a site of vascular injury.

REFERENCES

Albiero R et al., "Short- and intermediate-term results of $^{32}$P radioactive b-emitting stent implantation in patients with coronary artery disease." *Circulation* 101:18-26 (2000).

Barath P et al., *Cathet Cardiovasc Diagn, July* 1997, 41(3): 333-41.

Bartorelli A L et al., *Cathet Cardiovase Diag*, November 1997, 42(3):313-20.

Casterella P J et al, *Cardiol Rev*, July-August 1999, 7(4): 219-31.

Cleland J L, *Biotech Progress*, January-February 1998, 14(1):102-7.

Dev N B et al., *Cathet Cardiovasc Diagn*, November 1998, 45(3):337-45.

Dick A et al., *Cardiovasc Intervent Radiol*, September-October 1999, 22(5):389-93.

Drachman Del. et al., "Neointimal thickening after stent delivery of paclitaxel: change in composition and arrest of growth over six months." *J Am Coll Cardiol* 2000; 36:2325-32.

Edelman E R, Rogers C., "Pathobiologic responses to stenting." *Am J Cardiol* 1998, 81:4E-6E.

Fischman D L, Leon M B, Baim DS et al., "A randomized comparison of coronary stent placement and balloon angioplasty in the treatment of coronary artery disease." Stent Restenosis Study Investigators. *N Engl J Med.* 1994, 331: 496-501.

Gottman D et al., *Rofo Fortschr Geb Rontgenstr Neuen Bildgeb Verfahr*, Jan 1999, 170(1):84-8.

Herdeg C, Oberhoff M, Baumbach A et al., "Local Paclitaxel delivery for the prevention of restenosis: biological effects and efficacy in vivo." *J Am Coll Cardiol.* 2000; 35(7): 1969-76.

Herdeg C et al., *Cathet Cardiovasc Diagn*, July 1997, 41(3):308-14.

Herrmann S M et al., "Polymorphisms of the human matrix gla-protein gene (MGP); vascular calcification and myocardial infarction." *Arterioscler Thromb Vasc Biol* 2000; 20: 2836-93.

Hiatt B L et al., *Rev. Cardiovasc Medicine* 2(4):190-196 (2001).

Hodgkin D D et al., *J Cardiovasc Pharmacol*, January 1997, 29(1):39-44.

Iversen P. and Weller D., PCT Pubn. No. WO 00/44897, "Method of Treating Restenosis by Antisense Targeting of c-myc." (Aug. 3, 2000).

Kipshidze N., Keane D. et al., *Catheter Cardvac. Interv.* 54(2):247-56 (Oct 2001).

Koh W J et al., *Int J Radiat Oncol Biol Phys.*, Nov. 1, 1996, 36(4):829-34.

Kornowski R, Hong M K, Tio FO et al., "In-stent restenosis: contributions of inflammatory responses and arterial injury to neointimal hyperplasia." *J Am Coll Cardiol* 1998; 31:224-230.

Kreuter J, *J Anatomy, Dec* 1996, 189(Pt 3):503-5.

Kwon G S, *Crit Rev In Therap Drug Carrier Systems* 1998, 15(5):481-512.

Leon M B, Teirstein P S, Moses J W et al., "Localized intracoronary gamma-radiation therapy to inhibit the recurrence of restenosis after stenting." *N Engl J Med* 2001; 25; 344(4):250-6.

Malhotra S, Teirstein P S, "The SCRIPPS trial catheter-based radiotherapy to inhibit coronary restenosis." *J Invasive Cardiol.* 2000; 12(6): 330-32.

Oberhoff M et al., *Cathet Cardiovasc Diagn*, July 1997, 41(3):268-74.

Pavlides G S et al., *Cathet Cardiovasc Diagn*, July 1997, 41(3):287-92.

Porter T R et al., *J Ultrasound Med, Aug* 1996, 15(8):577.

Quintanar-Guerrero D et al., *Drug Dev Ind Pharm* December 1998, 24(12):1113-28.

Raman V K et al., *Semin Interv Cardiol*, September-December 1998, 3(3-4):133-7.

Ravi Kumar M N, *J Pharm & Pharm Sci* May-August 2000, 3(2):234-58.

Robinson K A et al., *Cathet Cardiovasc Diagn*, July 1997, 41(3):348-53.

Roy S et al., *J Vasc Interv Radiol* June 1999, 10(6):817-24.

Rubartelli P et al., *J Am Coll Cardiol*, July 1998, 32(1):90-6.

Savage M P et al., *J Am Coll Cardiol*, February 1998, 31(2):307-11.

Serruys P W, de Jaegere P, Kiemeneij F et al., "A comparison of balloon-expandable stent implantation with balloon angioplasty in patients with coronary artery disease." *N Eng J Med.* 1994, 331: 489-495.

Soppimath, Kans. et al., *J Controlled Release* Jan. 29, 2001, 70(1-2):1-20.

Suzuki T et al., "Stent-based delivery of sirolimus reduces neo-intimal formation in a porcine coronary model." *Circulation* Sep. 4, 2001;104(10):1188-93.

Teomim D et al., *J Controlled Release* Jun. 28, 1999, 60(1):129-42.

BACKGROUND OF THE INVENTION

Transluminal coronary angioplasty was introduced in the late 1970's as a nonsurgical treatment for obstructive coronary artery disease. Typically, the procedure involves placing a balloon-tip catheter at the site of occlusion, and disrupting and expanding the occluded vessel by inflating the catheter balloon. Since its introduction, major advances in equipment and techniques have led to widespread use of the method for treating coronary artery disease and angina. Recent studies have reported an equivalent seven-year survival rate for percutaneous transluminal coronary angioplasty (PTCA) and bypass surgery in patients with multivessel coronary artery disease. The process, however, damages the blood vessel wall, including loss of the endothelial lining of the vessel. Frequently the response to this injury includes myointimal hyperplasia, proliferation of fibroblasts, connective tissue matrix remodelling and formation of thrombus. These events lead to restenosis of the blood vessel, a segmentally limited, wound healing response to trauma of the vascular wall. This healing response leads to narrowing of the lumen of the vessel wall and hence to a high incidence (30 to 50%) of restenosis (Fischman et al., Serruys et al.).

Clinical trials in restenosis prevention using various revascularization devices, antiplatelet drugs, antithrombotic drugs, and anti-inflammatory agents have produced limited improvement in the incidence of restenosis. Attempts to improve the risk or severity of restenosis have employed intravascular stents (e.g. Savage, Rubarteli, Gottman), radiation therapy (Koh), and/or administration of anti-proliferative drugs at the vessel injury site. The latter approach typically employs the balloon catheter for introducing the therapeutic agent at the vessel occlusion site (Dick, Roy, Dev, Alfke, Robinson, Barath, Herdeg, Pavlides, Oberhoff, Hodgkin), or releasing drug from an implanted stent (Teomin, Bartonelli, Raman).

The use of coronary stent implantation has reduced the rate of angiographic restenosis to the low teens in large arteries. Coronary stents provide luminal scaffolding that virtually eliminates elastic recoil and remodeling. Stents, however, do not decrease neointimal hyperplasia and in fact lead to an increase in the proliferative comportment of restenosis (Edelman et al.).

Drug coated or drug impregnated stents deployed within the lumen of the blood vessel have been widely explored as drug delivery devices. The drug is gradually eluted from the stent and diffuses into the vessel wall from the intima. Examples of drugs used to coat stents include rapamycin (Sirolimus®, Wyeth Ayerst), a macrolide antibiotic with immunosuppressive properties, paclitaxel (Taxol®, Bristol-Myers Squibb), and actinomycin D, both chemotherapeutic agents. All of these have been shown to inhibit smooth muscle cell proliferation in such settings (Herdeg et al., 2000; Suzuki et al., 2001; Drachman et al., 2000; Hiatt et al., 2001).

However, with increased use of stent implantation, the frequency of in-stent restenosis also increases. There is evidence that the degree of inflammation and subsequent neointima formation is proportional to the degree of penetration of the vessel wall by the stent struts (Herdeg et al.). Regardless of treatment strategy (e.g. PTCA, rotational atherectomy, laser angioplasty, cutting balloon angioplasty, or repeat stenting), the restenosis in case of in-stent restenosis is unacceptably high (20 to 80%).

Other limitations of drug-eluting stents include limitation of drug loading capacity and poor control of drug elution, resulting in unreliable pharmacokinetics. The devices are typically coated with biocompatible polymers, and durability of the polymer coatings has been problematic. The thickness of some currently used coatings makes these devices unsuitable for very small vessels. Finally, most of the current coatings are prone to causing chronic inflammatory responses. Other long term effects of the devices can include late thrombosis, weakening of the vessel wall, or delayed restenosis. Thus, long term follow-up is necessary to monitor the polymer's potential toxicity. Treatment with coated stents can also be costly, especially in cases where a multi-stenting procedure is planned.

Intracoronary brachytherapy (Leon et al., Malhotra et al.) is a current approach to prevention of renarrowing of an artery after angioplasty or stent placement. A small amount of radiation is delivered to the treated area, either via catheter, which delivers radiation to the treated area and is then removed, or via a radiation-emitting stent, which remains in place. Although shown to be effective in reducing the need for additional treatment of in-stent restenosis, the procedure may be associated with other complications. Weeks to months after brachytherapy, restenosis may occur at the edges of the treatment areas. Low-level radiation that penetrates beyond the targeted treatment area increases the growth of the soft tissue, resulting in narrowing, which is known as the "candy wrapper" or "edge" effect (Albiero et al.). Such edge effects can also occur with drug-eluting stents, since the drug is not available beyond the edges of the stent.

Vascular occlusive phenomena also occur in other therapeutic settings. Autologous vein grafting, for example, is widely employed in coronary bypass procedures. About 400,000 to 500,000 first-time coronary graft procedures are performed every year in the United States alone. Although patient survival rates exceed 90% over the first five years after treatment, about 20% to 40% of the grafts fail during this time due to occlusive phenomena. Thus, 80,000-100,000 graft replacement procedures are needed in the U.S. yearly to avoid premature mortality.

Vascular occlusive phenomena also lead to failures in other vascular grafts, such as arterial-venous anastomosis used for kidney dialysis, and in organ transplants. In the vascular access model of kidney dialysis, a surgically formed arterial-venous anastomosis or shunt provides access to the artery and vein used for dialysis. During dialysis, the rate of blood flow, turbulence and stress at the venous junction is much higher than in a normal vein. Repeated exposure to these pressures frequently leads to hyperplasia and stenosis within the vein, causing dialysis access failure.

Accordingly, the incidence of restenosis, and the inability to predict the response to treatment, remains a serious risk factor in vascular angioplasty and other vascular surgical procedures.

SUMMARY OF THE INVENTION

The present invention includes, in one aspect, a method of inhibiting stenosis formation in a blood vessel. Such stenosis typically results, in the absence of treatment, from trauma to a vessel, such as an incision, an angioplasty procedure, or other excessive pressure. In accordance with the method, a composition comprising an antirestenotic compound conjugated to a microparticle carrier is administered to a site of trauma in the vessel. The antirestenotic compound is preferably an immunosuppressive or antiproliferative compound, preferably selected from the group consisting of rapamycin, tacrolimus, paclitaxel, and active analogs or derivatives thereof. The microparticle carrier comprises a suspension of insoluble gas-containing microbubbles or biocompatible polymeric microparticles in a pharmaceutically acceptable liquid vehicle. The microparticle carrier is effective to deliver the conjugated therapeutic to the site of vessel trauma. The composition may be administered prior to, during, and/or following a procedure selected from balloon angioplasty, stent implantation, and surgical incision or grafting of the vessel. In one embodiment, where the procedure comprises stent implantation, administration of the composition is effective to inhibit intrastent restenosis; that is, restenosis distal and proximal to the stent.

Preferably, the therapeutic compound is released at the site of trauma without application of external stimulation (such as ultrasound or heat) to the composition following administration.

In selected embodiments, the antirestenotic compound is selected from the group consisting of rapamycin, tacrolimus, paclitaxel, and active analogs or derivatives or prodrugs thereof. In one embodiment, the compound is rapamycin. The composition may further comprise, also conjugated to the microparticle carrier, an antiinflammatory compound, e.g. a steroid such as dexamethasone, and/or a compound effective to inhibit collagen accumulation or calcification of the vascular wall.

In one embodiment, the carrier is a suspension of insoluble gas-containing microbubbles, where the gas is preferably $SF_6$ or a perfluorocarbon gas such as perfluoromethane, perfluoroethane, perfluoropropane, perfluorobutane, or perfluoropentane. The liquid vehicle is preferably an aqueous vehicle containing at least one filmogenic compound selected from a protein, surfactant, lipid, polysaccharide, and combinations thereof. In one embodiment, the liquid vehicle is an aqueous solution of human serum albumin and dextrose.

In a related aspsect, the invention provides a method of inhibiting intrastent stenosis formation at regions proximal and distal to an implanted stent in a blood vessel, by administering to the vessel a composition comprising an antirestenotic compound conjugated to a microparticle carrier, where the carrier comprises biocompatible polymeric microparticles, or, preferably, a suspension of insoluble gas-containing microbubbles, such as perfluorocarbon gas-containing microbubbles, in a pharmaceutically acceptable liquid vehicle. The antirestenotic compound may be, for example, rapamycin, tacrolimus, paclitaxel, an active analog, derivative or prodrug of any of these, an antisense oligonucleotide having an antiproliferative effect, or a combination thereof. Administration may be carried out prior to, during, and/or following implantation of the stent, and is preferably carried out without application of external stimulation to the composition, during or following administration.

These and other objects and features of the invention will become more fully apparent when the following detailed description of the invention is read in conjunction with the accompanying drawings.

DETAILED DESCRIPTION OF THE INVENTION

Figure 1:
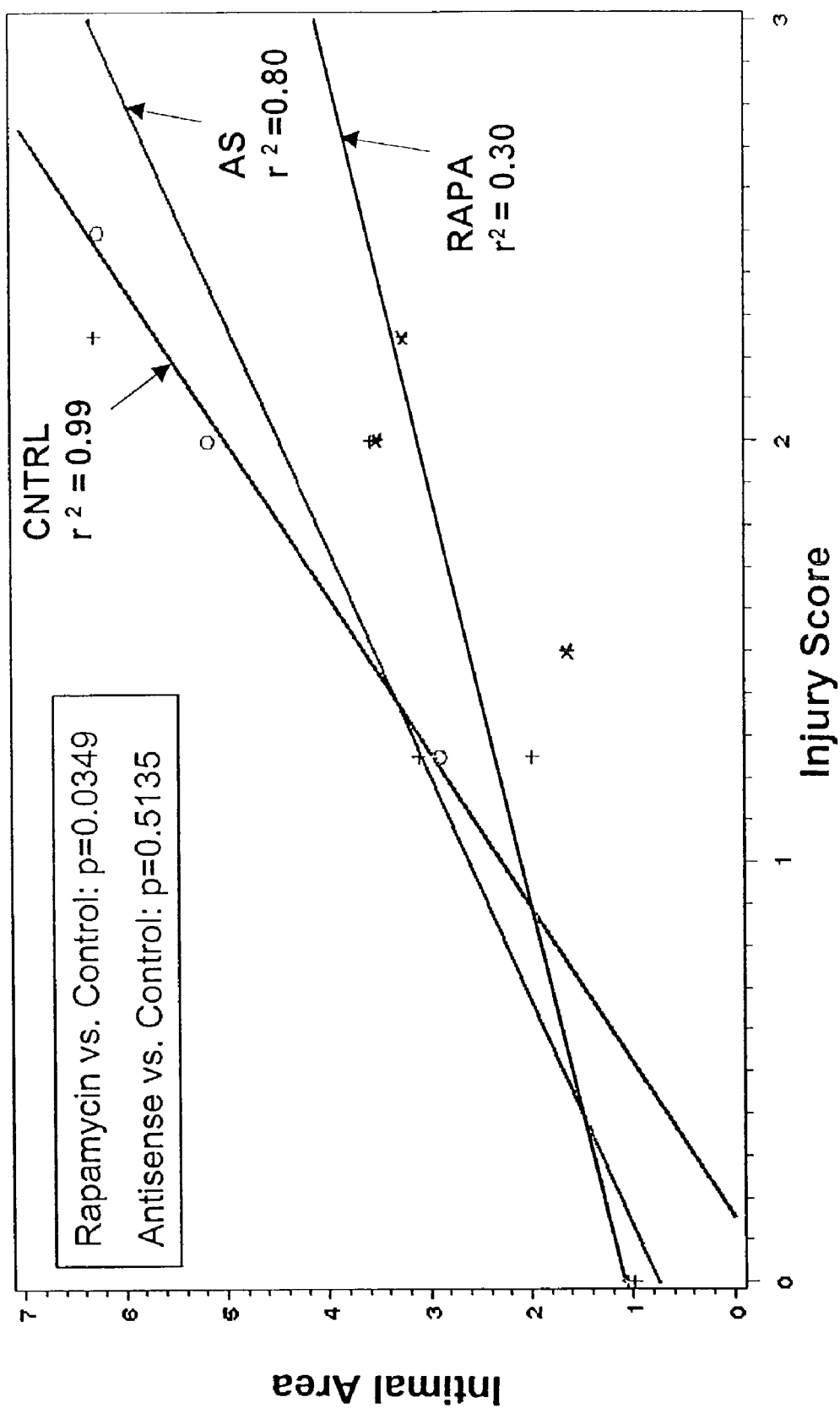
FIG. 1 is a regression plot of IA (Intimal Area) vs. IS (Injury Score) determined from histomorphometric analysis of vessels in three groups of pigs which underwent balloon angioplasty and stent implantation, followed by treatment with microbubble-conjugated rapamycin, microbubble-conjugated c-myc antisense, or vehicle control.

I. Therapeutic Compositions
  A. Carrier Compositions

The present therapeutic compositions comprise a drug which is conjugated to a microparticle carrier, such as a gaseous microbubble in a fluid medium or a polymeric microparticle, with sufficient stability that the drug can be carried to and released at a site of vascular injury in a subject. Such conjugation typically refers to noncovalent binding or other association of the drug with the particle, and may be brought about by incubation with a microbubble suspension, as described further below, or intimate mixing of the drug with a polymeric microparticle carrier. A "site of vascular injury" or "site of trauma" may be defined as any region of the vessel subjected to excessive pressure, incision, abrasion, or radiation, or other phenomena which would, in the absence of treatment, tend to result in the development of stenosis. Such sites are typically characterized by the presence of damaged vascular endothelium.

In one embodiment, the pharmaceutical composition comprises a liquid suspension, preferably an aqueous suspension, of microbubbles containing a blood-insoluble gas. The microbubbles are preferably about 0.1 to 10µ in diameter. Generally, any blood-insoluble gas which is nontoxic and gaseous at body temperature can be used. The insoluble gas should have a diffusion coefficient and blood solubility lower than nitrogen or oxygen, which diffuse in the internal atmosphere of the blood vessel. Examples of useful gases are the noble gases, e.g. helium or argon, as well as fluorocarbon gases and sulfur hexafluoride. Generally, perfluorocarbon gases, such as perfluoromethane, perfluoroethane, perfluoropropane, perfluorobutane, and perfluoropentane, are preferred. It is believed that the cell membrane fluidizing feature of the perfluorobutane gas enhances cell entry for drugs on the surface of bubbles that come into contact with denuded vessel surfaces, as described further below.

The gaseous microbubbles are stabilized by a fluid filmogenic coating, to prevent coalescence and to provide an interface for binding of molecules to the microbubbles. The fluid is preferably an aqueous solution or suspension of one or more components selected from proteins, surfactants, lipids, including phospholipids, and polysaccharides. In preferred embodiments, the components are selected from proteins, surfactant compounds, and polysaccharides. Suitable proteins include, for example, albumin, gamma globulin, apotransferrin, hemoglobin, collagen, and urease. Human proteins, e.g. human serum albumin (HSA), are preferred.

Conventional surfactants include compounds such as alkyl polyether alcohols, alkylphenol polyether alcohols, and alcohol ethoxylates, having higher alkyl (e.g. 6-20 carbon atom) groups, fatty acid alkanolamides or alkylene oxide adducts thereof, and fatty acid glycerol monoesters. Surfactants particularly intended for use in microbubble contrast agent compositions are disclosed, for example, in Nycomed Imaging patents U.S. Pat. No. 6,274,120 (fatty acids, polyhydroxyalkyl esters such as esters of pentaerythritol, ethylene glycol or glycerol, fatty alcohols and amines, and esters or amides thereof, lipophilic aldehydes and ketones; lipophilic derivatives of sugars, etc.), U.S. Pat. No. 5,990,263 (methoxy-terminated PEG acylated with e.g. 6-hexadecanoyloxyhexadecanoyl), and U.S. Pat. No. 5,919,434.

Other filmogenic synthetic polymers may also be used; see, for example, U.S. Pat. No. 6,068,857 (Weitschies) and U.S. Pat. No. 6,143,276 (Unger), which describe microbubbles having a biodegradable polymer shell, where the polymer is selected from e.g. polylactic acid, an acrylate polymer, polyacrylamide, polycyanoacrylate, a polyester, polyether, polyamide, polysiloxane, polycarbonate, or polyphosphazene, and various combinations of copolymers thereof, such as a lactic acid-glycolic acid copolymer.

Such compositions have been used as contrast agents for diagnostic ultrasound, and have also been described for therapeutic applications, such as enhancement of drug penetration (Tachibana et al., U.S. Pat. No. 5,315,998), as thrombolytics (Porter, U.S. Pat. No. 5,648,098), and for drug delivery (see below). The latter reports require some external method of releasing the drug at the site of delivery, typically by raising the temperature to induce a phase change (Unger, U.S. Pat. No. 6,143,276) or by exposing the microbubbles to ultrasound (Unger, U.S. Pat. No. 6,143,276; Klaveness et al., U.S. Pat. No. 6,261,537; Lindler et al., cited below, Unger et al., cited below; Porter et al., U.S. Pat. No. 6,117,858).

In one embodiment, the carrier is a suspension of perfluorocarbon-containing dextrose/albumin microbubbles known as PESDA (perfluorocarbon-exposed sonicated dextrose/albumin). Human serum albumin (HSA) is easily metabolized within the body and has been widely used as a contrast agent. The composition may be prepared as described in co-owned U.S. Pat. Nos. 5,849,727 and 6,117,858. Briefly, a dextrose/ albumin solution is sonicated while being perfused with the perfluorocarbon gas. The microbubbles are preferably formed in an $N_2$-depleted, preferably $N_2$-free, environment, typically by introducing an $N_2$-depleted (in comparison to room air) or $N_2$-free gas into the interface between the sonicating horn and the solution. Microbubbles formed in this way are found to be significantly smaller and stabler than those formed in the presence of room air. (See e.g. Porter et al., U.S. Pat. No. 6,245,747, which is incorporated by reference.)

The microbubbles are conjugated with rapamycin or another suitable immunosuppressive and/or antiproliferative drug, as described further below. Generally, the microbubble suspension is incubated, with agitation if necessary, with a liquid formulation of the drug, such that the drug non-covalently binds at the gas/fluid interface of the microbubbles. The incubation may be carried out at room temperature, or at moderately higher temperatures, as long as the stability of the drug or the microbubbles is not compromised. Preferably, the liquid formulation of the drug(s) is first filtered through a micropore filter and/or sterilized.

Drugs with limited aqueous solubility (such as rapamycin, tacrolimus, and paclitaxel) can be solubilized or intimately dispersed in pharmaceutically acceptable vehicles by methods known in the pharmaceutical arts. For example, rapamycin can be dissolved in, for example, alcohol, DMSO, or an oil such as castor oil or Cremophor™. A liquid formulation of rapamycin is also available from Wyett Ayerst Pharmaceuticals, and can be used, preferably after sterilization with gamma radiation. Other solubilizing formulations are known in the art; see, for example, U.S. Pat. No. 6,267,985 (Chen and Patel, 2001), which discloses formulations containing triglycerides and a combination of surfactants.

Other microbubble-therapeutic compositions are described in, for example, U.S. Pat. No. 6,143,276 (Unger) and U.S. Pat. No. 6,261,537 (Klaveness et al.), which are incorporated herein by reference. These references, as well as Lindler et al., *Echocardiography* 18(4):329, May 2001, and Unger et al., *Echocardiography* 18(4):355, May 2001, describe use of the microbubbles for therapeutic delivery of the conjugated compounds, in which the compounds are released from the microbubbles by application of ultrasound at the desired point of release. As described herein, neither ultrasound, nor other external stimulation, was required for delivery of therapeutically effective amounts of rapamycin to damaged endothelium in angioplasty-injured coronary vessels.

In addition to gas-filled microbubbles, other microparticles, such as biocompatible polymeric particles, may be used for delivery of a conjugated drug, e.g. rapamycin, to damaged endothelium, since very small particles tend to adhere to denuded vessel surfaces (i.e. vessels having damaged endothelium).

In this sense, "nanoparticles" refers to polymeric particles in the nanometer size range (e.g. 50 to 750 nm), while "microparticles" refers to particles in the micrometer size range (e.g. 1 to 50μ), but may also include particles in the submicromolar range, down to about 0.1μ. For use in the methods described herein, a size range of about 0.1 to 10μ is preferred. Such polymeric particles have been described for use as drug carriers into which drugs or antigens may be incorporated in the form of solid solutions or solid dispersions, or onto which these materials may be absorbed or chemically bound. See e.g. Kreuter 1996; Ravi Kumar 2000; Kwon 1998. Methods for their preparation include emulsification evaporation, solvent displacement, "salting-out", and emulsification diffusion (Soppimath et al.; Quintanar-Guerrero et al.), as well as direct polymerization (Douglas et al.) and solvent evaporation processes (Cleland).

Preferably, the polymer is bioerodible in vivo. Biocompatible and bioerodible polymers that have been used in the art include poly(lactide-co-glycolide) copolymers, polyanhydrides, and poly(phosphoesters). Poly(orthoester) polymers designed for drug delivery, available from A.P. Pharma, Inc., are described in Heller et al., *J. Controlled Release* 78(1-3): 133-141 (2002). In one embodiment, the polymer is a diol—diol monoglycolide—orthoester copolymer. The polymer can be produced in powdered form, e.g. by cryogrinding or spray drying, intimately mixed in powdered form with a therapeutic compound, and fabricated into various forms, including microspheres and nanospheres.

B. Therapeutic Compounds

The therapeutic compositions include at least one antirestenotic agent, preferably and immunosuppressive and/or antiproliferative drug, conjugated to and delivered by the carrier composition described above. Examples of drugs with significant antiproliferative effects include rapamycin, paclitaxel, other taxanes, tacrolimus, angiopeptin, flavoperidol, actinomycin D, and active analogs, derivatives or prodrugs of these compounds. Also included are antisense oligonucleotides having antiproliferative effects, such as oligonucleotides effective to inhibit expression of genes encoding enzymes which mediate smooth muscle proliferation. Oligonucleotides antisense to c-myc may be used, and are described in co-owned and copending application having U.S. Ser. No. 09/493,427, which is hereby incorporated by reference.

Other therapeutic agents that may be used beneficially include antiinflammatory compounds, such as dexamethasone and other steroids; vassenoids; hormones such as estrogen; matrix metalloprotienase inhibitors; protease inhibitors; lipid lowering compounds; ribozymes; vascular, bone marrow and stem cells; diltiazem; acridine; clopidogrel; antithrombins; anticoagulants, such as heparin or hirudin; and genetic material, e.g. antisense agents. Also included are antioxidants; antiplatelets, such as aspirin, halofuginore, or IIBIIIA antagonists; antibiotics; calcium channel blockers; converting enzyme inhibitors; cytokine inhibitors; growth factors; growth factor inhibitors; growth factor sequestering agents; tissue factor inhibitors; smooth muscle inhibitors; organoselenium compounds; retinoic acid and other retinoid compounds; sulfated proteoglycans; superoxide dismutase mimics; NO; NO precursors; and combinations thereof.

In particular, synthetic glucocorticoids such as dexamethasone decrease the inflammatory response to vessel injury and may eventually decrease the restenotic process. The compositions of the invention may also include agents, preferably in combination with an antiproliferative agent, that inhibit collagen accumulation and/or calcification of the vascular wall. For example, local delivery of Vitamin K has been reported to counteract the calcification effect associated with vessel injury (Herrmann et al., 2000). Agents believed to function via different "antirestenotic mechanisms" may be expected to act synergistically. It may be useful, therefore, to combine two or more of these agents; e.g. to combine an antiproliferative and/or immunosuppressive agent with an antiinflammatory and/or an anticalcification agent.

The therapeutic agent conjugated to the microparticles is preferably selected from the group consisting of rapamycin (sirolimus), tacrolimus (FK506), paclitaxel (Taxol), epothilone D, fractionated or unfractionated heparin, and flavoperidol, as well as active analogs or derivatives, such as prodrugs, of these compounds. More preferably, it is selected from the group consisting of rapamycin, tacrolimus, and paclitaxel, as well as active analogs or derivatives, such as prodrugs, of these compounds.

In a preferred embodiment, the agent is rapamycin. Rapamycin (available under the trade name Rapamune®) is a macrocyclic lactone produced by *Streptomyces hygroscopicus*, found in the soil of Easter Island. Structurally, it resembles tacrolimus and binds to the same target, an intracellular binding protein or immunophilin known as FKBP-12. Accordingly, other molecules which bind this target are also considered. Rapamycin is reported to function by blocking IL2-dependent T-lymphocyte proliferation and the stimulation caused by cross-linkage of CD28, possibly by blocking activation of a serine-threonine kinase that is important for cell cycle progression.

II. Treatment Method

Restenosis refers to the renarrowing of the vascular lumen following vascular intervention, such as coronary artery balloon angioplasty with or without stent insertion. It is clinically defined as greater than 50% loss of initial luminal diameter gain following the procedure. Restenosis is believed to occur in about 30% to 60% of lesions treated by angioplasty and about 20% of lesions treated with stents within 3 to 6 months following the procedure. (See, e.g., Dev).

Stenosis can also occur after a coronary artery bypass operation, wherein heart surgery is done to reroute, or "bypass," blood around clogged arteries and improve the supply of blood and oxygen to the heart. In such cases, the stenosis may occur in the transplanted blood vessel segments, and particularly at the junction of replaced vessels. As noted above, stenosis can also occur at anastomotic junctions created for dialysis.

The present invention is directed to methods for reducing the risk (incidence) or severity (extent) of stenosis, particularly following balloon angioplasty and/or stent implantation, or in response to other vessel trauma, such as following an arterial bypass operation or hemodialysis. More generally, the invention is directed to methods to prevent, suppress, or treat hyperproliferative vascular disease. The method includes administering to the affected site, the above-described microbubble- or microparticle-conjugated therapeutic agent(s), in an amount effective to reduce the risk and/or severity of hyperproliferative disease. Administration may take place before, during, and/or after the procedure in question, and multiple treatments may be used. The administration may be via a route such as systemic i.v., systemic intraarterial, intracoronary, e.g. via infusion catheter, or intramural, i.e. directly to the vessel wall. When the therapeutic agent is rapamycin, preferred doses are typically between about 0.05-20 mg/kg, more preferably about 0.1 to 5.0 mg/kg. In another preferred embodiment, about 50-400 mg rapamycin per $cm^2$ of affected area is administered.

The therapeutic agents are conjugated to the microparticle carrier, preferably a microbubble composition, alone or in combination. The carrier delivers the agent or agents to the site of vessel damage, where, in a preferred embodiment, the agent is released without the use of external stimulation. As described below, delivery of rapamycin to a site of vessel injury via microbubbles did not require the use of external ultrasound, nor did it rely on a phase change in the microbubble fluid, as has been described in the prior art. However, if desired, release of the agent may also be modulated by application of a stimulus such as light, temperature variation, pressure, ultrasound or ionizing energy or magnetic field. Application of such a stimulus may also be used to convert a prodrug to the active form of the drug, which is then released.

Delivery of the compound via the above-described microparticles is effective to achieve high localized concentration of the compound at the vessel injury site, by virtue of adherence of the microparticles to damaged endothelium. By delivering drug to sites with incomplete endothelial lining, the method should be effective to treat small or branching vessels inaccessible by conventional routes, in addition to treating beyond the boundaries of coated stents.

The use of drug-coated stents has been associated with intrastent (proximal or distal to the stent) stenosis. For example, in a recently conducted multicenter double blind randomized study with rapamycin coated stents (Cordis J&J Bx Velocity), intrastent restenosis was observed in 9% of subjects. This effect is believed to be due to vessel injury that occurs, during stent implantation, in vessel segments adjacent to the stent. Various factors, such as the length of the balloon delivery system (which is always longer than the actual stent), manipulation of the guidewire, and the use of predilation balloon angioplasty, as well as operator error or improper stent length relative to the lesion, can contribute to such injury. In general, no diffusion of drug occurs from a drug-eluting stent (where the drug is, for example, rapamycin, paclitaxel, or tacrolimus) to the adjacent vessel wall, proximal and distal to the implanted stent. Therefore, no antirestonic drug is available in these areas, which are prone to intrastent restenosis phenomena. A similar effect, known as the edge effect or "candy wrapper" effect, is often observed after vascular brachytherapy (vascular radiation therapy, which often follows balloon angioplasty and/or stent implantation).

Delivery of an antirestenotic compound, as described herein, via the above-described microparticles is thus advantageously used in combination with stent implantation and/or brachytherapy, since the compositions of the invention extend treatment beyond the boundaries of the stent. Microparticle delivery of the drug before treatment, immediately after treatment, or later in time can prevent or reduce the complications described above and greatly improve results obtained from implantation of a drug-eluting (or radiation-emitting) stent.

III. In vivo Studies

As shown below, rapamycin conjugated to PESDA and administered intravenously showed evidence of penetration into damaged vessels four hours after balloon angioplasty and administration of the composition, and significantly reduced arterial stenosis, in comparison to a control group and a c-myc antisense treated group.

In the study, described in detail in the Materials and Methods section below, seven immature farm pigs were divided into acute and chronic treatment groups. The two acute animals were treated with balloon angioplasty followed by implantation of stents in three separate coronary vessels. One received PESDA microbubbles with rapamycin (2 mg total dose) adsorbed, and the other received PESDA microbubbles with an antisense c-myc agent adsorbed. The antisense agent was a phosphorodiamidate-linked morpholino oligomer (see e.g. Summerton and Weller, *Antisense Nucleic Acid Drug Dev.* 7:63-70, 1997) having the sequence 5'-ACGT-TGAGGGGCATCGTCGC-3', which is targeted to the ATG translation site of c-myc mRNA (see Iversen and Weller, PCT Pubn. No. WO 00/44897).

A. Acute Effects

The pigs were sacrificed four hours after treatment, and vessel tissue was examined for expression of p21, p27, β-actin and c-myc. Rapamycin enhances the expression of p21 and p27 and should have no effect on β-actin. The antisense c-myc should inhibit the expression of myc, with no effect on β-actin and minimal effect on p21 or p27. Hence, administration of c-myc antisense represents a control for rapamycin treatment, and the rapamycin represents a control for c-myc antisense agent.

Western blot analysis of p21, p27 and β-actin expression was determined by densitometry of bands appearing at the appropriate molecular weight. The band density of p21 relative to β-actin and p27 relative to β-actin are provided in the table below: (LCX=left circumflex artery; LAD=left anterior descending; RCA=right coronary artery)

TABLE 1

| Vessel | p21/β-actin ratio | | p27/β-actin ratio | |
| --- | --- | --- | --- | --- |
| | Rap/PESDA | PMO/PESDA | Rap/PESDA | PMO/PESDA |
| LCX | 0.714 | 0.221 | 1.251 | 0.421 |
| LAD | 1.001 | 0.229 | 3.348 | 1.864 |
| RCA | 0.931 | 0.788 | 0.624 | 0.622 |

These data show that vessels treated with rapamycin carried by microbubbles have elevated expression of both p21 and p27, the anticipated effect of rapamycin. The 2 mg dose in 35-40 kg pigs is too small for this effect to be due to systemic accumulation of rapamycin at the injured vessel site. This provides evidence that the microbubbles effectively carry the rapamycin to the site of vessel injury and deposit the rapamycin at the injury site.

B. Chronic Effects

The remaining 5 pigs were treated with balloon angioplasty and stent implantation, then divided into (1) control (no drug treatment), (2) rapamycin/PESDA treatment and (3) antisense c-myc/PESDA treatment. Pigs were sacrificed 4 weeks after treatment for analysis of tendency for restenosis. The endpoint for these studies included quantitative angiography and histomorphometry, as described in Materials and Methods below. Histomorphometry data at 28 days post procedure, measured as described in the Examples below, are given in Tables 2 and 3, below.

No evidence of myocardial infarction was seen on gross inspection or after histological evaluation. H&E and VVG-stained sections of all arterial segments were examined. All stents were well developed within the vessel, resulting in thinning of the media adjacent to the stent struts. In the rare vessels with stent protrusion into the adventitia, there was evidence of perivascular hemorrhage. No cases of thrombosis of the treated segment were observed in any of the treatment groups. Complete healing was observed with virtually no toxicity in the treatment groups, and re-endothelialization was complete in all treatment groups.

Neointima from treated arteries was smaller in size than the controls. Control arteries exhibited a substantial neointima, consisting mostly of stellate and spindle-shaped cells, in a loose extracellular matrix. In the antisense treated arteries, the cells of the neointima were morphologically similar to the controls.

Table 2 shows control and rapamycin data for individual vessels. Note that the restenosis process reduces the lumen area and increases the intimal and medial area. Units are in mm and mm².

TABLE 2

| Vessel - Trtmt | Lumen Area | Intimal Area | Medial Area |
| --- | --- | --- | --- |
| LAD - rapa 661 | 4.62 ± 1.01 | 3.26 ± 2.18 | 1.52 ± 0.31 |
| LAD - rapa 662 | 8.04 ± 1.59 | 2.94 ± 1.26 | 1.85 ± 0.05 |
| LAD - control | 3.55 ± 0.92 | 2.89 ± 0.93 | 1.43 ± 0.18 |
| RCA - rapa 661 | 7.45 ± 0.32 | 1.64 ± 0.55 | 2.08 ± 0.51 |
| RCA - control | 2.54 ± 1.14 | 6.24 ± 1.15 | 1.87 ± 0.42 |
| LCX - rapa 661 | 2.23 ± 1.57 | 3.53 ± 1.40 | 1.02 ± 0.23 |

Both measurements for LAD lumen area are larger in the rapamycin coated microbubble group than in the control groups (4.62 and 8.04 vs. 3.55), and the RCA lumen area is also much larger than in the control (8.04 vs. 2.54). Although, in this study, the rapamycin treatment did not significantly alter medial area or intimal thickening in the LAD, intimal thickening was greatly reduced in the RCA (1.64 vs.6.24).

Table 3 shows averaged histomorphometric data from measurements of the individual vessels. For control, n=3; for rapamycin, n=4-6, and for antisense, n=6. Values for the first ten variables (arterial diameter—lumen area) are in mm or mm². Grading systems described by Komowski et al. and by Suzuki et al. (*Circulation* 104(10):1188-93, 2001) were used to assess the vessel wall and extent of vascular repair (intimal vascularity; intimal fibrin; intimal SMC content; adventitial fibrosis).

Injury score (IS) and inflammation score were adapted from the scoring system described by Komowski et al., who observed that implanted stents cause neointimal proliferation proportional to injury. The ratio of ncointimal area/injury score (IA/IS) provides a normalized value of intimal area related to the extent of vessel injury. The values of Intimal Thickness and Intimal Area, as well as the normalized values of IA/IS, show that both therapeutic compositions inhibited stenosis relative to the control, with the rapamycin composition significantly superior to the c-myc composition. This is also illustrated in FIG. 1, a regression plot of IA vs. IS for the three treatment groups.

TABLE 3

| Variable | Control | Rapamycin | c-myc Antisense |
| --- | --- | --- | --- |
| Arterial Area | 9.70 ± 1.58 | 10.04 ± 2.59 | 10.94 ± 2.09 |
| Intimal Area (IA) | 4.77 ± 1.71 | 1.84 ± 0.44 | 2.83 ± 1.99 |
| Media Area | 1.60 ± 0.24 | 1.62 ± 0.46 | 1.83 ± 0.45 |
| Int/Med Ratio | 3.02 ± 0.80 | 2.11 ± 1.25 | 1.81 ± 1.59 |
| Lumen Area | 3.34 ± 0.72 | 6.55 ± 1.69 | 6.07 ± 3.20 |
| Area % Occl. | 57.53 ± 13.19 | 26.00 ± 19.00 | 33.26 ± 24.63 |
| Lum/Art Ratio | 0.35 ± 0.11 | 0.65 ± 0.16 | 0.55 ± 0.20 |
| Injury Score (IS) | 1.92 ± 0.63 | 1.75 ± 0.46 | 1.13 ± 0.96 |
| IA/IS | 2.48 | 1.05 | 2.50 |
| Inflam Score | 0.67 ± 0.52 | 0.44 ± 0.13 | 0.17 ± 0.30 |
| Intimal Vascularity | 0.42 ± 0.52 | 0.38 ± 0.48 | 0.17 ± 0.30 |
| Intimal Fibrin | 0.17 ± 0.14 | 0.19 ± 0.24 | 0.21 ± 0.25 |
| Intimal SMC Content | 3.00 ± 0.00 | 3.00 ± 0.00 | 3.00 ± 0.00 |
| Adventitial Fibrosis | 1.17 ± 0.76 | 0.88 ± 0.25 | 0.71 ± 0.62 |

IEM = internal elastic lamina;
SMC = smooth muscle cell

Materials and Methods

Rapamycin/PESDA

PESDA microbubbles were prepared as described in, for example, U.S. Pat. No. 6,245,747 and PCT Pubn. No. WO 2000/02588. In a typical procedure, 5% human serum albumin and 5% dextrose, obtained from commercial sources, are drawn into a 35 mL syringe in a 1:3 ratio, hand agitated with 6-10 mL of decafluorobutane, and sonicated at 20 kilohertz for 75-85 seconds. As described in U.S. Pat. No. 6,245,747, the mean size of four consecutive samples of PESDA microbubbles produced in this manner, as measured with hemocytometry, was 4.6±0.4 microns, and mean concentration, as measured by a Coulter counter, was $1.4 \times 10^9$ bubbles/mL.

A solution of rapamycin in a pharmaceutically acceptable solvent, such as alcohol, DMSO, or castor oil, was incubated with agitation with the PESDA microbubble suspension at room temperature. The mixture was allowed to settle, with the rapamycin-conjugated microbubbles rising to the top. If necessary, the rapamycin solution is sterilized and/or filtered through a micropore filter prior to incubation.

Animals and Experimental Protocol

Animals received humane care in compliance with the "Principles of Laboratory Animal Care" formulated by the National Society for Medical Research and the "Guide for the Care and Use of Laboratory Animals" prepared by the National Academy of Sciences and published by the National Institutes of Health (NIH publication #85-23, revised 1985).

Seven female or male juvenile pigs (25 to 30 kg) were sedated with a combination of ketamine (20 mg/kg) and xylazine (2 mg/kg) by intramuscular injection. The animals were given pentobarbital (10-30 mg/kg IV) and were subsequently intubated and ventilated with oxygen (2 L/min) and isoflurane 1% (1.5 L/min) using a respirator. Adequate anesthesia was confirmed by the absence of a limb withdrawal reflex. Limb-lead electrocardiography and blood pressure (Honeywell E for M) were monitored throughout the procedure.

After placement of an 8F-introducer sheath in the right carotid artery by surgical cutdown, each animal received heparin (150 units/kg). Under fluoroscopic guidance, an 8F guiding catheter was positioned in the left or right coronary ostium. Coronary angiography was performed after intracoronary nitroglycerin (200 µg) administration and recorded on cine film (Phillips Cardiodiagnost; Shelton, Conn.).

Stent Implantation

Coronary stenting was performed at the site of delivery using V-Flex stents 15 mm in length (Cook Inc., Bloomington, Ind.), hand crimped on the balloon and deployed at high pressure (10-14 Atm×30 sec). The stents were mounted on a balloon 3.5-4.0 mm in diameter and 20 mm in length. The stent artery ratio was kept between 1:1.1-1:1.2. Immediately postprocedure, angiograms were performed to assess vessel patency; the carotid sheath was removed, the carotid artery ligated, the skin closed and the animal allowed to recover. All animals were pretreated with aspirin 325 mg and ticlopidine 250 mg BID, 24 hours prior to the procedure until sacrifice.

Efficacy of Rapamycin Delivery Into Tissues

To evaluate the impact of rapamycin delivery upon p21 and p27 expression following stent implantation, two juvenile pigs weighing 30-35 kg underwent oversized multiple stent implantation (3 per animal) in the coronary artery. This was followed by i.v. injection of rapamycin/PESDA complex (2 mg rapamycin). Four hours after the procedure, the pigs were sacrificed, and injured tissues were analyzed by western blot for p21 and p27 expression.

Chronic Studies

The remaining 5 pigs were treated with balloon angioplasty and stent implantation, as described above, and divided into (1) control (no drug treatment), (2) rapamycin/PESDA treatment (2 mg rapamycin) and (3) antisense c-myc/PESDA treatment. At four weeks the animals were sacrificed. The arteries were perfusion-fixed and the injured segments, located with the guidance of the coronary angiograms, were dissected free from the heart. The segment was fixed in 10% formalin solution and embedded in paraffin or a cold polymerizing resin (Technovit 7100; Heraus Kulzer GmbH, Wehrheim, Germany). Cross-sections (5 µm) were stained with hematoxylin and eosin (H&E) and Verhoeff van-Giesson elastin (VVG) stain.

Histological and Morphometric Analysis

Histomorphometric analysis was performed on each segment with evidence of medial fracture. The histomorphometric parameters were measured on 5-8 sections per vessel, averaged and expressed as mean value±SD. Vessel sections were measured by an experienced investigator who was unaware of the treatment group assignment.

The histopathological features were measured using a computerized PC-compatible image analysis program (Optimas 6; Optimas, Inc., Bothell, Wash.). VVG-stained sections were magnified at 7.5×, digitized, and measured in a framegrabber board (DAGE-MTI, Mich. City, Ind.). Area measurements were obtained by tracing the lumen perimeter (luminal area, LA, $mm^2$), medial perimeter (medial area, MA, $mm^2$), neointima perimeter (intimal area, IA, $mm^2$, defined by the borders of the internal elastic lamina, lumen, media, and external elastic lamina), and external elastic lamina (vessel area, VA, $mm^2$).

Injury score and inflammation score were adapted from the scoring system described by Kornowski et al., *J. Am. Coll. Cardiol.* 31:224-30 (1998), and the grading scheme of Kornowski et al. and Suzuki et al. (*Circulation* 104(10):1188-93, 2001) was used to assess the vessel wall and extent of vascular repair.

Endothialization was scored on the basis of percent of the intimal surface covered by endothial cells: (1) 0-25%; (2) 25-75%, and (3)>75%.

Intimal fibrin content was graded based on the following criteria: (1) focal residual fibrin involving any portion of the artery; moderate fibrin deposition adjacent the stent strut involving <25% of the circumference of the vessel; (2) moderate fibrin deposition involving >25% of the circumference of the vessel; (3) heavy fibrin deposition involving <25% of the circumference of the vessel.

Intimal SMC content was graded based on the following criteria: (1) sparse SMC density involving any portion of the artery; moderate SMC infiltration less than the full thickness of the neointima involving <25% of the circumference of the vessel; (2) moderate SMC infiltration less than the full thickness of the neointima involving >25% of the circumference of the vessel or dense SMC content the full thickness of the neointima involving <25% of the circumference of the vessel; (3) dense SMC content the full thickness of the neointima involving >25% of the circumference of the vessel.

After artery removal, hearts were sectioned transaxially at 1 cm intervals and examined for evidence of myocardial damage.

Statistical Evaluation

Data (mean±standard deviation) were analyzed for overall differences between treatment groups using one-way ANOVA with the Bonferroni correction. Comparison of the mean values with a p value of less than 0.05 was considered statistically different. All statistics were performed using SPSS 10.0 for Windows (SPSS, Inc. Chicago, Ill.). The intimal area and injury score were correlated using linear regression analysis.

While the invention has been described with reference to specific methods and embodiments, it will be appreciated that various modifications may be made without departing from the invention.

It is claimed:

1. A method of inhibiting stenosis formation in vivo at a site of trauma in a blood vessel, comprising:
    administering to said vessel in vivo a composition comprising an antirestenotic compound conjugated to a microparticle carrier;
    wherein the antirestenotic compound is selected from the group consisting of rapamycin, active analogs or derivatives or prodrugs thereof, and combinations thereof, and the microparticle carrier comprises an aqueous suspension of insoluble gas-containing microbubbles,
    and wherein said composition is effective to inhibit stenosis formation in vivo at said site of trauma.

2. The method of claim 1, wherein said administration is carried out prior to, during, and/or following a procedure selected from balloon angioplasty, stent implantation, and surgical incision or grafting of the vessel.

3. The method of claim 1, wherein a single intravenous administration of said composition is effective to inhibit stenosis formation in vivo at said site of trauma.

4. The method of claim 3, wherein the procedure comprises stent implantation, and said administration is effective to inhibit intrastent restenosis.

5. The method of claim 1, wherein said administration is carried out without application of external stimulation to said composition during or following administration.

6. The method of claim 1, wherein the antirestenotic compound is rapamycin.

7. The method of claim 1, wherein the composition further comprises, conjugated to said carrier, an antiinflammatory compound, a compound effective to inhibit collagen accumulation or calcification of the vascular wall, or a combination thereof 8. The method of claim 1, wherein the gas is $SF_6$ or a perfluorocarbon gas.

9. The method of claim 8, wherein the gas is selected from perfluoromethane, perfluoroethane, perfluoropropane, perfluorobutane, and perfluoropentane.

10. The method of claim 1, wherein the aqueous suspension contains at least one filmogenic compound selected from a protein, surfactant, lipid, polysaccharide, and combinations thereof 11. The method of claim 6, wherein the carrier is a suspension of perfluorocarbon gas-containing microbubbles in an aqueous vehicle.

12. The method of claim 11, wherein the aqueous vehicle comprises at least one filmogenic compound selected from a protein, surfactant, lipid, polysaccharide, and combinations thereof.

13. The method of claim 12, wherein the vehicle contains human serum albumin and dextrose.

14. A method of inhibiting intrastent stenosis formation in vivo, at regions proximal and distal to an implanted stent in a blood vessel, comprising:
    administering to a vessel in vivo in which such a stent is implanted, a composition comprising an antirestenotic compound conjugated to a microparticle carrier, wherein the microparticle carrier comprises an aqueous suspension of insoluble gas-containing microbubbles,
    and the antirestenotic compound is selected from the group consisting of rapamycin, active analogs or derivatives or prodrugs thereof, and combinations thereof,
    wherein said administering is effective to inhibit intrastent stenosis formation.

15. The method of claim 14, wherein said administration is carried out prior to, during, and/or following implantation of the stent.

16. The method of claim 14, wherein said administration is carried out without application of external stimulation to said composition during or following administration.

17. The method of claim 14, wherein the carrier is a suspension of perfluorocarbon gas-containing microbubbles in an aqueous vehicle.

18. The method of claim 1, wherein said composition is administered by intravenous injection.

* * * * *

UNITED STATES PATENT AND TRADEMARK OFFICE
CERTIFICATE OF CORRECTION

| | | |
|---|---|---|
| PATENT NO. | : 7,754,238 B2 | Page 1 of 1 |
| APPLICATION NO. | : 10/190419 | |
| DATED | : July 13, 2010 | |
| INVENTOR(S) | : Patrick L. Iversen et al. | |

It is certified that error appears in the above-identified patent and that said Letters Patent is hereby corrected as shown below:

Column 15, Line 33
"thereof" should read, --thereof.--.

Column 16, Line 4
"thereof" should read, --thereof.--.

Signed and Sealed this
Thirty-first Day of May, 2011

David J. Kappos
*Director of the United States Patent and Trademark Office*